US00PP17191P2

(12) United States Plant Patent
Harris

(10) Patent No.: US PP17,191 P2
(45) Date of Patent: Nov. 7, 2006

(54) ***AZALEA* PLANT NAMED 'MNIELE'**

(50) Latin Name: ***Rhododendron* sp.**
Varietal Denomination: MNIELE

(76) Inventor: James O. Harris, 538 Swanson Dr., Lawrenceville, GA (US) 30043

( * ) Notice: Subject to any disclaimer, the term of this patent is extended or adjusted under 35 U.S.C. 154(b) by 31 days.

(21) Appl. No.: 11/180,480

(22) Filed: Jul. 13, 2005

(51) Int. Cl.
*A01H 5/00* (2006.01)

(52) U.S. Cl. ..... Plt./240
(58) Field of Classification Search ..... Plt./240, Plt./238
See application file for complete search history.

*Primary Examiner*—Kent Bell
(74) *Attorney, Agent, or Firm*—Jondle & Associates P.C.

(57) ABSTRACT

A new variety of *Azalea* plant found as a seedling in a planned cross between the female *Azalea* 'Delos' and the male *Azalea* 'Dorothy Clark' is disclosed. The new variety is an upright, open natured plant with attractive evergreen foliage, and very large and unique, single, bi-colored flowers that fall off clean.

2 Drawing Sheets

Genus/species: *Rhododendron* sp.
Botanical designation: 'MNIELE'.

BACKGROUND OF THE INVENTION

The present invention is a new and distinct variety of evergreen *Azalea* of the genus *Rhododendron*. This new *Azalea,* hereinafter referred to as 'MNIELE', was discovered in March, 1999 in Lawrenceville, Ga. 'MNIELE' originated from a planned cross hybridization between hybrid *Azalea* 'Delos' (unpatented) and hybrid *Azalea* 'Dorothy Clark' (unpatented) in Lawrenceville, Ga. The value of this new cultivar lies in its bloom color, bloom size, growth habit, foliage and cold hardiness.

Asexual propagation of the new plant by cuttings was performed in Dearing, Ga. The new plant retains its distinctive characteristics and reproduces true to type in successive generations by vegetative propagation.

SUMMARY OF THE INVENTION

The following are the most outstanding and distinguishing characteristics of this new cultivar when grown under normal horticultural practices in Dearing, Ga.

1. Large, showy bi-color flowers;
2. Large, single flower;
3. Easily propagated by semi-hardwood cuttings in late spring through summer;
4. Flowers fall off clean;
5. Upright, open, and spreading nature;
6. Attractive foliage;
7. Grows well in containers;
8. Thrives in shade or sun;
9. Hardy in USDA Zone 7a.; and
10. Occasionally re-blooming in fall.

DESCRIPTION OF THE PHOTOGRAPHS

This new *Azalea* hybrid variety is illustrated by the accompanying photographs which show blooms and foliage of the plant in full bloom. The colors shown are as true as can be reasonably obtained by conventional photographic means.

Figure 1:
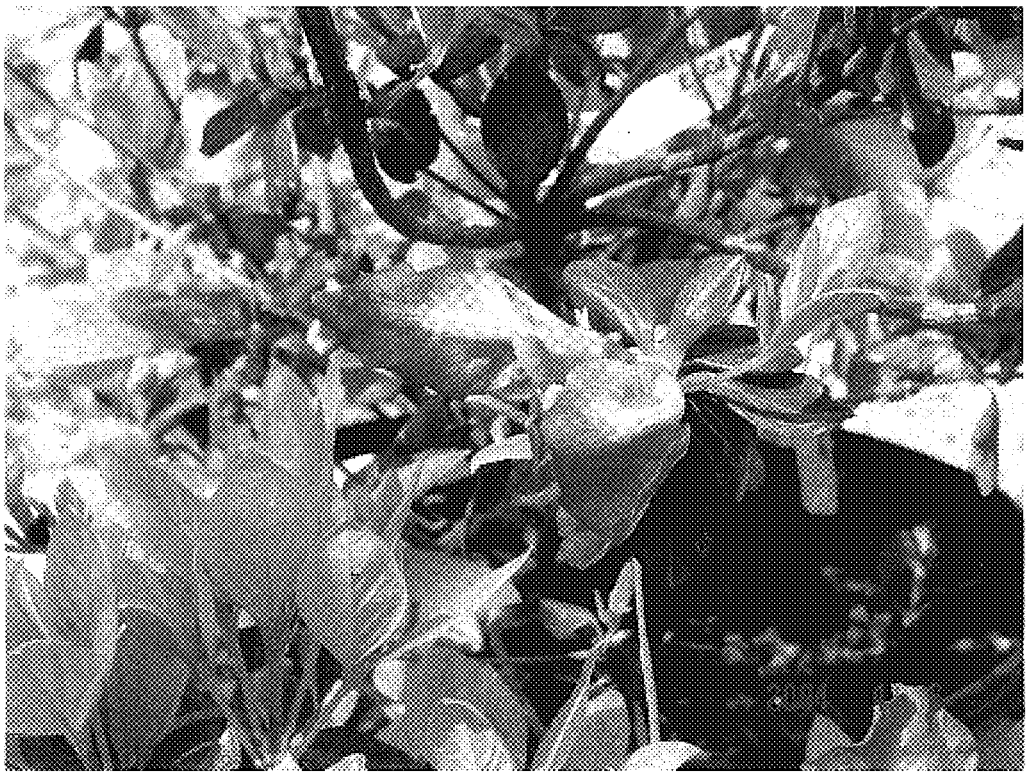

FIG. 1. shows a close-up view of flower buds, immature foliage, and stems.

Figure 2:
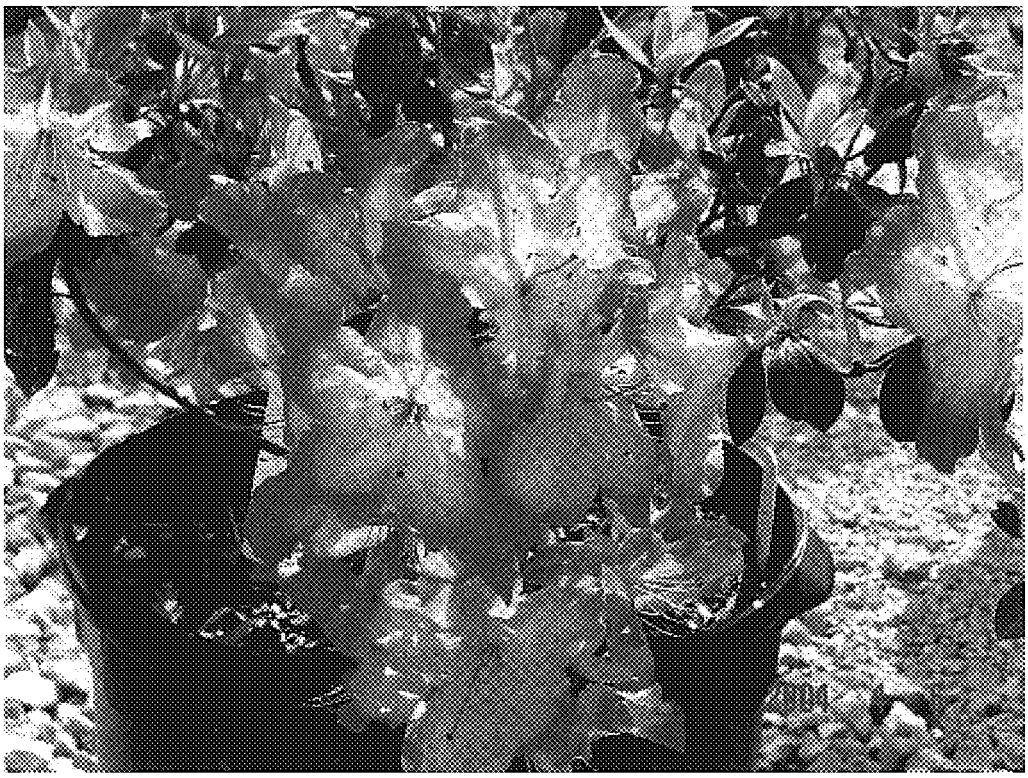

FIG. 2. shows several mature inflorescences.

Figure 3:
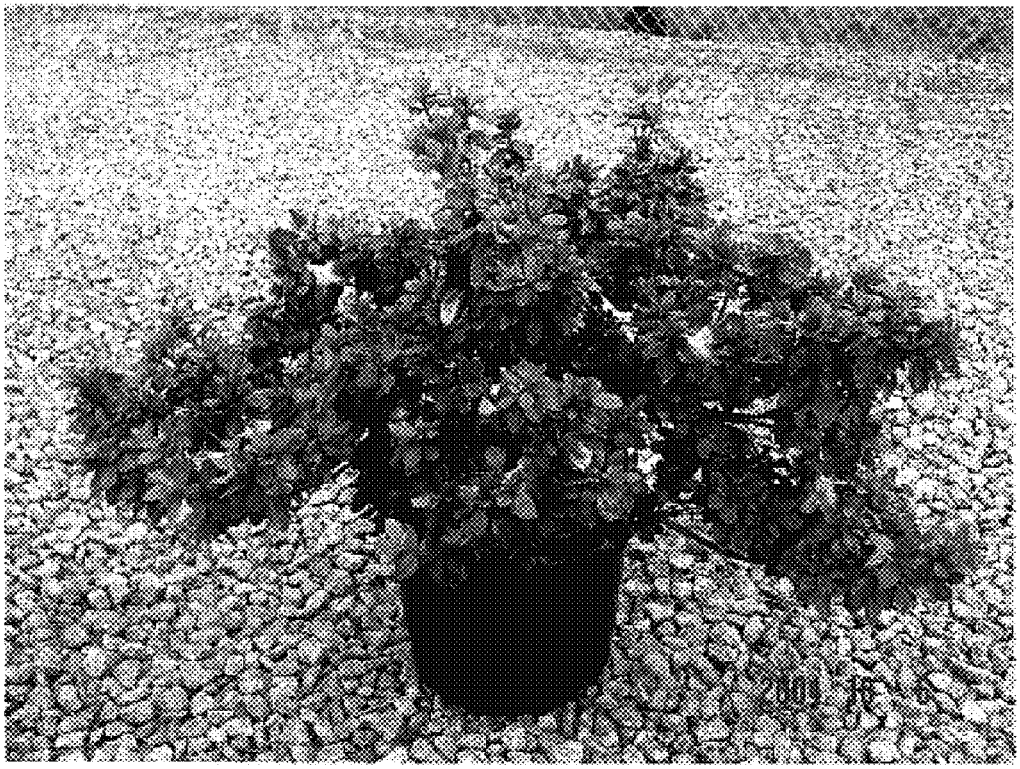

FIG. 3. shows mature foliage and growth habit of a seven-gallon plant.

Figure 4:
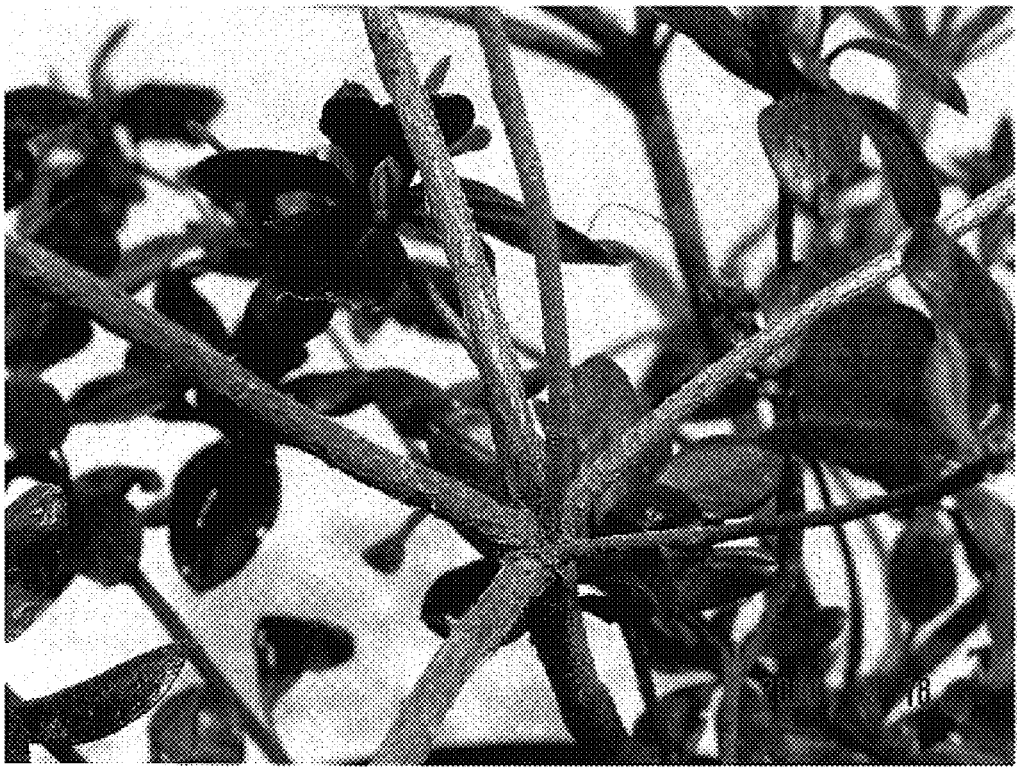

FIG. 4. shows a close-up view of stems.

DETAILED DESCRIPTION OF THE NEW PLANT

The following is a detailed description of the new variety of *Azalea* based on observations made of a 3 year-old plant grown in a seven-gallon container according to wholesale commercial production conditions in Dearing, Ga. The colors of the various plant parts are detailed with reference to The Royal Horticultural Society Colour Chart.

Classification:
- *Family*.—Ericaceae.
- *Species*.—*Rhododendron* sp.
- *Common name*.—*Azalea*.
- *Commercial name*.—'MNIELE'.

Parentage:
- *Female parent*.—Glenn Dale hybrid *Azalea* 'Delos' (unpatented).
- *Male parent*.—Harris hybrid *Azalea* 'Dorothy Clark' (unpatented).

Growth:
- *Form*.—Open and spreading.
- *Height*.—12–18 inches.
- *Width*.—4–5 feet.
- *Growth habit*.—Upright, open, and spreading.
- *Growth rate*.—Fast growth rate under normal fertilization and moisture conditions. In a period of six years from a rooted cutting, the plant reaches a height of 24–36 inches and a spread of 3 feet. The growth rate is normally about 4 to 6 inches per year; the plant reaches a height of 48 to 72 inches at maturity.
- *Spring growth*.—In 2004, the date of initial spring growth was March 16, in Dearing, Ga. After the initial spring flush, there was continuous growth through the fall. The average length of terminal growth of the initial spring flush is about 3 inches for a plant in full sun and and about 3¼ inches when grown in shade. This growth, if not pruned, will begin to produce flowers starting in late March. The remaining growth produces about 2 to 3 inches of new growth.

*Life cycle.*—Perennial and evergreen.

Leaves: Leaves are evergreen.

*Leaf arrangement.*—Alternate, simple.

*Leaf shape.*—Broadly elliptic.

*Leaf length.*—2½ inches.

*Leaf width.*—1¼ inches.

*Leaf margin.*—Entire.

*Leaf base.*—Acuminate.

*Leaf apex.*—Mucronate.

*Petiole length.*—3/16 inch.

*Petiole color.*—RHS 146C (yellow-green).

*Mature leaf.*—Upper leaf surface: Surface texture: Semi-glossy. Surface color: RHS 147A (yellow-green). Surface pubescence: Slight. Surface pubescence color: FHS 164B (greyed-orange). Midveins and laterals: Impressed on surface. Lower leaf surface: Surface texture: Matte. Surface color: RHS 146B (yellow-green). Surface pubescence: Slight. Surface pubescence color: RHS N163C (greyed-orange). Midveins and laterals: Prominent on surface.

*Immature leaf.*—Upper leaf surface: Surface texture: Matte. Surface color: RHS 144A (yellow-green). Surface pubescence: Strigose and Scabrous. Surface pubescence color: RHS 168D (greyed-orange). Lower leaf surface: Surface texture: Matte. Surface color: RHS 146C (yellow-green). Surface pubescence: Strigose. Surface pubescence color: RHS 155C (white). Immature petioles and midveins: Petiole color: RHS 146C (yellow-green). Midvein color: RHS 146C (yellow-green). Petiole pubescence: Strigose. Petiole pubescence color: RHS 168D (greyed-orange). New growth pubescence: Strigose, scabrous. Length of pubescence: 1/32 inch; numerous on mid-vein and petiole.

Stems:

*Young stems.*—Stem color: RHS 144B (yellow-green). Stem pubescence: Strigose. Stem pubescence color: at point of attachment individual hairs emerge RHS 155C (white) and mature to RHS 167A (greyed-orange); hairs distal from stem are RHS 164C (greyed-orange). Stem length: 3 to 6 inches. Stem diameter: ⅛ to 3/16 inch.

*Second-year stems.*—Stem color: RHS 199A (greyed-brown) and RHS 197B (greyed-green). Stem pubescence: Strigose. Stem pubescence color: RHS 166C (greyed-orange). Stem length: 3 to 6 inches. Stem diameter: 3/16 to ¼ inch.

*Pith.*—Solid and uniform.

*Internode length.*—Grown in full sun: ⅛ inch to ⅞ inch; Grown in light shade: ⅛ to ¾ inch.

Flower buds:

*Buds.*—Tight; borne in groups of 2 to 3, sheathed by a pair of modified leaf bracts.

*Bud shape.*—Ovate.

*Bud size.*—⅝×¼ inch.

*Bud scale.*—Distal portion pubescent, individual hairs emerge RHS 155C (white) and mature to RHS N165B (greyed-orange).

*Bud color.*—RHS 145B (yellow-green) and RHS N34C (orange-red).

*Bud sheath.*—Bud sheath length: ½ to 1 inch. Immature sheath color: RHS 147A (yellow-green). Mature: As the buds swell, the bud sheath matures to RHS 174A (greyed-orange), RHS 165B and RHS 145D (yellow-green), falls off and reveals the flower color of RHS 54A, RHS 55C, and RHS 56A.

*Bud pedicel.*—Pedicel length: ¼ to ½ inch. Pedicel color: RHS 153A (yellow-green). Pedicel pubescence: Strigose. Pedicel pubescence color: RHS 164C (greyed-orange).

*Calyx.*—Calyx shape: Cup-shaped, 5 sepals. Size: ⅜ inch long. Color: RHS 145A (yellow-green). Pubescence: Strigose. Color of pubescence: RHS 164D (greyed-orange).

Flowers:

*Flower type.*—Single, perfect.

*Flowering habit.*—Borne on the current season's growth.

*Lastingness of flowers on the plant.*—5–6 days in the garden, then fall off clean.

*Length of flowering period.*—2 to 3 weeks in late March and early April in Dearing, Ga. Occasional re-blooming from September until frost.

*Peduncle length.*—¼ inch.

*Peduncle diameter.*—3/16 inch.

*Flower shape.*—Open funnel-shaped.

*Flower diameter.*—4½ to 5½ inches.

*Petal number.*—5 fused at the base and remain fused up to 1¼ inches from the base.

*Petal pubescence.*—Glabrous.

*Petal shape.*—Orbicular with rounded apices and undulate margins.

*Petal size.*—2 inches long by 2 inches wide.

*Petal color.*—Upper and lower surfaces: RHS 54A (red) near border, RHS 55C and RHS 56A (red) in the center. Spots on upper surfaces of 3 of the five petals: RHS 53B (red) and RHS 165C (greyed-orange).

*Sepals.*—Ovate and joined at the base to form a cup.

*Sepal number.*—5.

*Sepal color.*—RHS 145A (yellow-green).

*Sepal size.*—⅜ inch long×3/16 inch wide.

Reproductive organs:

*Ovary.*—Densely villous.

*Placenta arrangement.*—12 locules.

*Pistil.*—Single, non-petaloid.

*Pistil length.*—2⅛ inches long.

*Stigma color.*—RHS 46A (red).

*Style color.*—RHS 58D, RHS 68D, and RHS 58A (red-purple).

*Stamen number.*—8 non-petaloid.

*Stamen length.*—1¾ inches.

*Stamen color.*—Filaments: RHS 56D (red). Anthers: RHS 170A (greyed-orange).

*Pollen color.*—RHS 4D (yellow).

*Fragrance.*—None.

CULTURE

'MNIELE' grows well in a wide range of conditions and tolerates sun to shade. It prefers moist, well-drained soil that is rich in organic matter and responds well to mulching and medium applications of fertilizer. It does best in soil with a pH of 5.0 to 5.5. It is propagated with semi-hardwood cuttings in late Spring through the Summer.

DISEASES/INSECTS

Lace bugs and spider mites can be a problem.

COMPARISON WITH PARENTAL CULTIVARS

The female, or seed parent of 'MNIELE' is the Glenn Dale hybrid *Azalea* 'Delos' (unpatented) which has light purplish pink, double flowers, is a mid-season bloomer, and is an erect to spreading grower. 'Delos' is the result of a cross between the white or purplish red blooming Chinese *Azalea* 'Vittata Fortunei' (unpatented) and the deep purplish pink blooming Satsuki hybrid 'Warai-Jishi' (unpatented).

The male, or pollen, parent is Harris hybrid 'Dorothy Clark' (unpatented) which has light pink with light red border, single flowers, is a mid-season bloomer, and is an upright grower. 'Dorothy Clark' is the result of a cross between the vivid pink blooming Glenn Dale hybrid #87 'Grace Freeman' (unpatented) and the vivid red blooming Satsuki hybrid 'Amagasa' (unpatented).

In Table 1 below, the instant plant is shown in comparison with the parental cultivars.

TABLE 1

| Characteristic | 'MNIELE' | 'Delos' | 'Dorothy Clark' |
|---|---|---|---|
| Height (Mature) | 48–72 inches | 6 ft. | 3 ft. |
| Width (Mature) | 4–5 ft. | 6 ft. | 3 ft. |
| Flower Diameter | 4½ to 5½ in. | 2½ in. | 4½ in. |
| Flower Form | Single | Double | Single |
| Flower Color | Red | Light purplish-pink | Light pink center, Light red border |
| Flowers per Terminal | 2 to 3 | 2 | 2 |
| Bloom Period | Late March to Mid-April, occasionally reblooms from September until frost | Mid-April | Mid to Late April |
| Petal Number | 5 | 15 | 5 |
| Hardy Zone | 7a | 7 | 7 |
| Stamen Number | 8 | 0–1 | 10 |
| Stamen Type | Non-petaloid | Petaloid | Non-petaloid |

What is claimed is:

1. A new variety of *Azalea* plant named 'MNIELE' as herein shown and described.

* * * * *